United States Patent [19]
Bello et al.

[11] 4,326,851
[45] Apr. 27, 1982

[54] LEVEL SENSOR APPARATUS AND METHOD

[75] Inventors: Ernesto Bello, Miami Springs; Steven N. Kolber, North Miami Beach; Wallace H. Coulter, Miami Springs, all of Fla.

[73] Assignee: Coulter Electronics, Inc., Hialeah, Fla.

[21] Appl. No.: 200,142

[22] Filed: Oct. 24, 1980

[51] Int. Cl.³ .................... G01N 1/14; G01N 35/06
[52] U.S. Cl. .................... 23/230 R; 422/63; 422/64; 422/100; 73/864.24; 73/864.25; 141/198
[58] Field of Search .................... 422/100, 63, 64; 141/130, 198; 73/423 A, 425.6, 427, 864.24, 864.25; 23/230 R; 204/1 T

[56] References Cited

U.S. PATENT DOCUMENTS

| | | | |
|---|---|---|---|
| 3,635,094 | 1/1972 | Oberli | 73/864.24 |
| 3,894,438 | 7/1975 | Ginsberg | 73/864.24 |
| 4,228,831 | 10/1980 | Kerns | 422/100 X |
| 4,235,840 | 11/1980 | Mendoza et al. | 422/100 X |
| 4,276,051 | 6/1981 | Ginsberg et al. | 422/64 X |
| 4,276,260 | 6/1981 | Drbal et al. | 422/64 X |

*Primary Examiner*—Ronald Serwin
*Attorney, Agent, or Firm*—Silverman, Cass & Singer, Ltd.

[57] ABSTRACT

A level sensor of a fluid transfer mechanism for determining when the bottom tip of a fluid aspirating probe touches or contacts the top surface of a sample fluid. The level sensor senses the contact capacitively by grounding one plate of a capacitor through the sample fluid and fluid aspirating probe. One capacitor plate is formed of an electrode biased against the bottom of a rotatable supply tray and positioned under a sample containing cavity in the tray. The other capacitor plate is formed by the bottom surface of the sample fluid in the supply cavity, and the dielectric of the capacitor is formed of the supply tray material. An AC signal is applied to the electrode and the probe is grounded. The change in voltage occurring in the AC signal at the electrode when the probe touches the top surface of the sample fluid it is sensed to provide the touch signal.

36 Claims, 5 Drawing Figures

LEVEL SENSOR APPARATUS AND METHOD

CROSS REFERENCE TO RELATED APPLICATIONS

This invention is related to the subject matter disclosed in the following copending and commonly assigned applications which are incorporated herein by reference:

Apparatus For Monitoring Chemical Reactions and Employing Moving Photometer Means, G. Ginsberg et al, Ser. No. 846,337, filed Oct. 28, 1977, now U.S. Pat. No. 4,234,538 issued Nov. 18, 1980.

Sample and Stat Feeding System and Sample Tray, G. Ginsberg et al, Ser. No. 115,924, filed Jan. 28, 1980, now U.S. Pat. No. 4,276,258 issued June 30, 1981.

Cuvette Washing Apparatus, B. Hodgins et al, Ser. No. 115,692, filed Jan. 28, 1980, now pending.

System and Program for Chemical Reaction Observation with a Moving Photometer, G. Ginsberg et al, Ser. No. 115,734, filed Jan. 28, 1980, now U.S. Pat. No. 4,276,051 issued June 30, 1981.

Fluid Transfer Mechanism, V. Drbal et al, Ser. No. 115,691, filed Jan. 28, 1980, now U.S. Pat. No. 4,276,260 issued June 30, 1981.

Probe Washer, B. Hodgins, Ser. No. 115,625, filed Jan. 28, 1980, now abandoned.

Variable Stop Syringe, B. Hodgins et al, Ser. No. 115,624, filed Jan. 28, 1980, now U.S. Pat. No. 4,278,086, issued July 14, 1981.

Optical Timing and A/D Conversion Method and Apparatus, Steven N. Kolber et al., Ser. No. 177,092, filed Aug. 11, 1980, now allowed.

BACKGROUND OF THE INVENTION

The invention relates to a level sensing apparatus and method for a fluid transfer mechanism transferring aliquots of conductive sample fluids from a supply to reaction vessels. More particularly, this invention relates to an apparatus and method for determining when the bottom tip of a fluid aspirating probe touches or makes contact with the upper surface of a sample fluid contained in a supply cavity.

Fluid transfer mechanisms are known which aspirate a precise aliquot or portion of a sample fluid from a supply in one location and dispense the aspirated aliquot in a reaction vessel located at another location. Such a device disclosed in the referenced application FLUID TRANSFER MECHANISM, V. Drbal, Ser. No. 115,691, filed Jan. 28, 1980, has the capability of transferring the desired fluid aliquot at a high rate of speed and with very precise positioning of a fluid aspirating and despensing probe in the vertical and horizontal directions.

It is important in such fluid transfer mechanisms that only the tip of the fluid aspirating probe be in contact with the sample fluid to be aspirated to avoid the sample probe carrying undesired quantities of the sample fluid on the exterior thereof. The reactions which are performed with the sample fluids usually concern or are performed to determine the condition of a patient's health and as such the quantity of the sample fluids which are used in the reactions must be precisely and accurately controlled. Undesired excess quantities on the exterior of the probe may affect reactions and provide misleading data concerning the condition of the patient's health.

The use of capacitive sensing in the detection of fluid levels is known, but in an apparatus where stray capacitance is of an order as great or greater than the capacitance involved in the sensing operation problems arise. This will occur where the liquid sample is extremely small as contemplated by the chemical analyzer mentioned. For instance the operator may upset data or sensing information by merely having his hand in the vicinity of the fluid transfer device.

SUMMARY OF THE INVENTION

The above and other disadvantages of prior level sensing apparatus and methods are overcome in accordance with the invention by forming a capacitor one plate of which is an electrode biased against the bottom surface of a rotatable supply tray and positioned under an individual supply cavity, the other plate of which is the bottom surface of the sample fluid contained in that individual cavity and whose dielectric is the material of the sample tray. The electrode has an AC signal applied thereto the modulation of which is sensed to determine when contact is made. The fluid probe is connected to the signal ground so that the AC signal on the electrode is capacitively ground when the probe touches the conductive fluid sample top surface. This modulates the AC signal which is sensed to provide the level sense signal.

DESCRIPTION OF THE PREFERRED EMBODIMENT

The level sensor apparatus and method are described with reference to a chemical reaction analyzer having high speed fluid transfer mechanisms transferring aliquots of electrically conductive sample fluids from a supply to reaction vessels. The level sensing apparatus and method are used to determine when the probe of the high speed fluid transfer mechanism has made contact with the top surface of the sample fluid or the interface between the sample fluid and the atmosphere. Although described in connection with the high speed fluid transfer mechanism, the level sensor apparatus and method of the present invention will find utility with any fluid level sensing apparatus and method.

Figure 1:
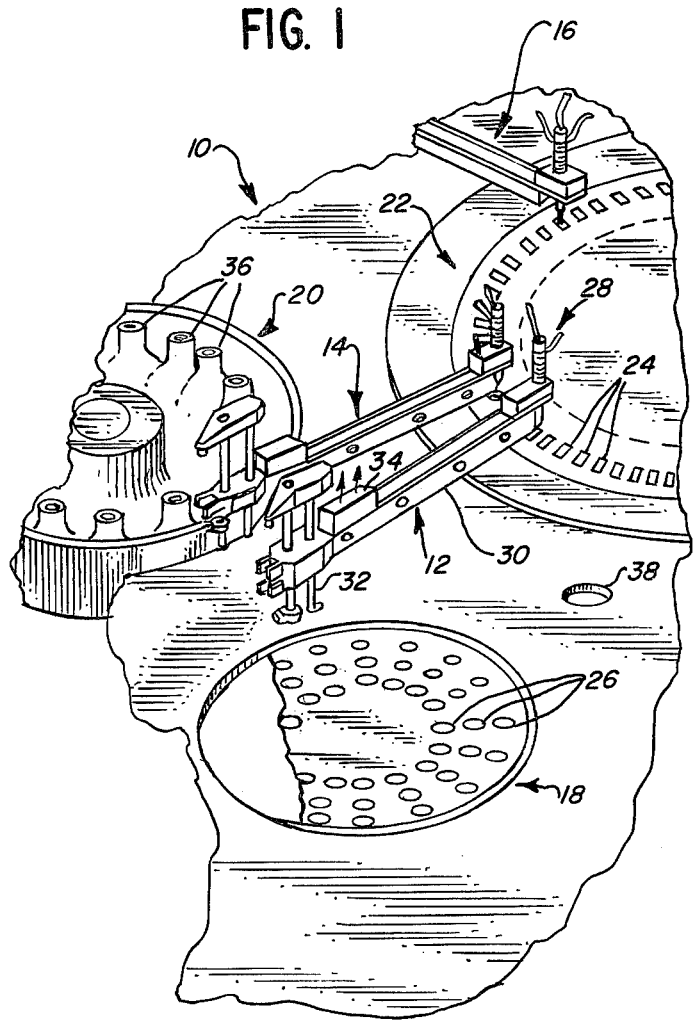
FIG. 1 is a fragmentary perspective view of a fluid transfer mechanism of a chemical analyzer.

Referring to FIG. 1, a chemical reaction analyzer is indicated generally by the reference character 10. Chemical reaction analyzer 10 includes three transfer mechanisms 12, 14, 16 and further includes a sample supply 18, reagent supply 20 and reaction rotor 22.

In analyzer 10, sample aliquots of sample fluids are picked up or aspirated by the mechanism 12 from the sample supply 18 and moved to and dispensed in the cuvettes 24 of the reaction rotor 22. The sample aliquots are mixed with first reagent aliquots which are aspirated and dispensed by the mechanism 14 from the supply 20. A second reagent aliquot may be added to the reaction cuvettes 24 by the third mechanism 16 from the supply 20 or from a different supply (not shown). The sample supply 18 may include samples, stats, controls and blanks which are aspirated from the sample supply in a predetermined order and then analyzed in the cuvettes 24. The cuvettes 24 preferably form a renewable supply by being cleaned in the analyzer 10 before arriving again at sample dispensing positions of the mechanisms 12, 14 and 16.

The sample supply 18 has a plurality of supply cavities or vessels 26 in which the samples, stats, controls and blanks are placed and contained. Supply 18 is rotatable and is rotated to align individual cavities 26 with pick up positions located along an arc defined by a fluid probe 28 carried by the transfer mechanism 12.

The probe 28 is carried at the end of an arm 30 cantilevered on a shaft or shafts 32. Transfer mechanism 12 is illustrated with probe 28 in a dispensing position with probe 24 inserted in one of the cuvettes 24 in the reaction rotor 22. The fluids aspirated from the sample supply 18 will be dispensed into the reaction cuvettes 24 and will be mixed therein by a motor 34 oscillating the arm 30 and moving probe 28 back and forth inside the cuvettes 24.

The transfer mechanism 14 operates in a similar manner to aspirate a fluid from one of a plurality of reagent containers 36 in the supply 20. The transfer mechanism 16 may aspirate a second reagent quantity from the reagent containers 36 or from another supply or row of containers (not shown).

The fluid probe 28 is swung or rotated about the vertical axis of shaft 32 to aspirate and dispense fluid quantities during its fluid transfer cycles. The types of supplies as well as the reaction cuvette array are illustrative and the transfer mechanisms 12, 14 and 16 may aspirate and dispense fluids from any position along arcs defined by the vertical axis of the respective vertical shafts of those transfer mechanisms. The fluids which are aspirated and dispensed by any one transfer mechanism may be different for each operation cycle of the transfer mechanism and it is very important that carry-over and contamination are eliminated since the fluids are related to tests upon the body fluids of a particular patient and carry-over and contamination could provide misleading data as to the condition of the patient's health.

There are essentially four steps or operations which are taken or performed by fluid transfer mechanism 12 during each fluid transfer cycle. These four operations are described in connection with transfer mechanism 12, and it will be understood that these same or similar steps or operations are used for each of transfer mechanisms 14 and 16, as desired. In the first step or aspirate operation, the probe 28 is in a rest position above a probe washer opening 38 and is swung to a position above one of the cavities 26. The probe 28 then is driven downwardly into the cavity until it contacts the top surface of the sample fluid or the interface between the fluid and atmosphere, at which time the downward motion of fluid probe 28 stops and probe 28 aspirates a desired precise aliquot of sample fluid.

During the second step or dispense operation, the fluid probe 28 is driven upwardly to the rotation position above the supply 18 and is swung to a position above one of the cuvettes 24. The fluid probe 28 then is driven downwardly into the cuvette 24 at which time the aspirated fluid aliquot is dispensed and the probe is oscillated to mix the fluids in the cuvette.

During the third step or wash operation, the fluid probe 28 is driven upwardly to its rotating position and is swung to a position above the probe washer opening 38. Fluid probe 26 then is driven down into the probe washer opening 38 wherein the fluid probe 28 is washed both internally and externally and dried. During the fourth step, fluid probe 28 is driven upwardly to its rest position above the probe washer opening 38.

In one chemical analyzer 10 utilizing the above cycle, the cuvettes 24 are stepped by the reaction rotor 22 one position every six seconds and hence each of the fluid transfer mechanisms 12, 14 and 16 performs all of the above steps or operational movements in less than six seconds. Thus, it is extremely critical that every one of the positions both vertical and rotational must be precisely and quickly attained by the fluid probes.

Figure 2:
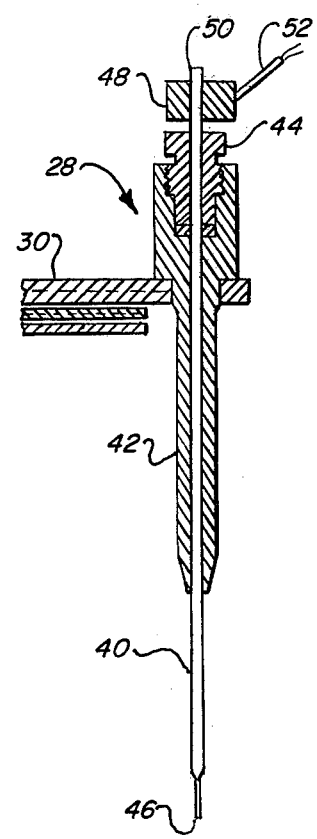
FIG. 2 is a median sectional view through a fluid probe used in the invention.

Referring to FIG. 2, fluid probe 28 is formed of a stainless steel aspiration and dispensing tube 40 mounted in a non-conductive sleeve 42 by a threaded fitting 44. The tube 40 includes a bottom tip 46 which has a fluid aspirating and dispensing opening therein and the tube 40 also serves as one lead of a capacitive level sensing circuit described hereinafter. Electrical connection to tube 40 is made by a block 48 which is welded or otherwise electrically connected to an upper end 50 of the tube 40 and includes an electrical lead 52 connected in a conventional matter. The upper end 50 of the tube 40 will have a fluid tubing connected thereto which is used to aspirate and dispense the sample aliquots into and out of the tube 40 by way of low and high pressures, respectively.

It is important in aspirating precise aliquots from the supply cavities 26 that the tip 46 of the fluid probe 28 just make contact with the sample fluids and is not inserted down into the sample fluid. In this way, the sample fluids will not wet the exterior of the tube 40 and there will not be undesired excess quantities of sample fluid carried on the exterior of tube 40. Thus, it is necessary to sense precisely and repeatably the vertical position at which the tip 46 of probe 28 just touches the top surface of the sample fluid or at which the tip 46 just touches the interface between the sample fluid and the atmosphere. For the same reasons, it is important to sense precisely when the tips of the fluid probes carried by the transfer mechanisms 14 and 16 contact the top surfaces of the reagents. Moreover, this level sensing must be performed for varying heights of the top surfaces of the sample fluids and reagents as aliquots are aspirated therefrom.

Sensing the top surfaces or fluid/atmosphere interfaces of the reagents is sufficiently performed by sensing the change in voltage of an electrical circuit occurring when the tip of a probe contacts the fluid top surface. In the reagent supply, there are large glass bottles and large steel pans or trays which provide large capacitive values available for sensing. These capacitive values are large in relation to stray capacitances which occur in analyzer 10. Thus, at the reagent supply 20, a capacitive level sensing apparatus and method may provide a fifty to seventy-five percent change in voltage values in a circuit which is used to sense the contact of the probe tip with the fluid surface. That provides sufficient values to precisely and repeatable sense the contact or touching.

In the sample supply 18, however, the capacitance values which are available to sense the contact between the probe tip and fluid top surface are much smaller than the stray capacitances. Thus, the electrical circuit sensing the capacitive change when the probe tip touches the sample fluid top surface senses only about a five percent change in voltage. This five percent change in voltage is not sufficient to sense precisely and repeatably the probe tip contact with the fluid surface. Accordingly, for the sample supply 18, a level sensing apparatus and method is required which is more sensitive than that used for the reagent supply 20.

Figure 3:
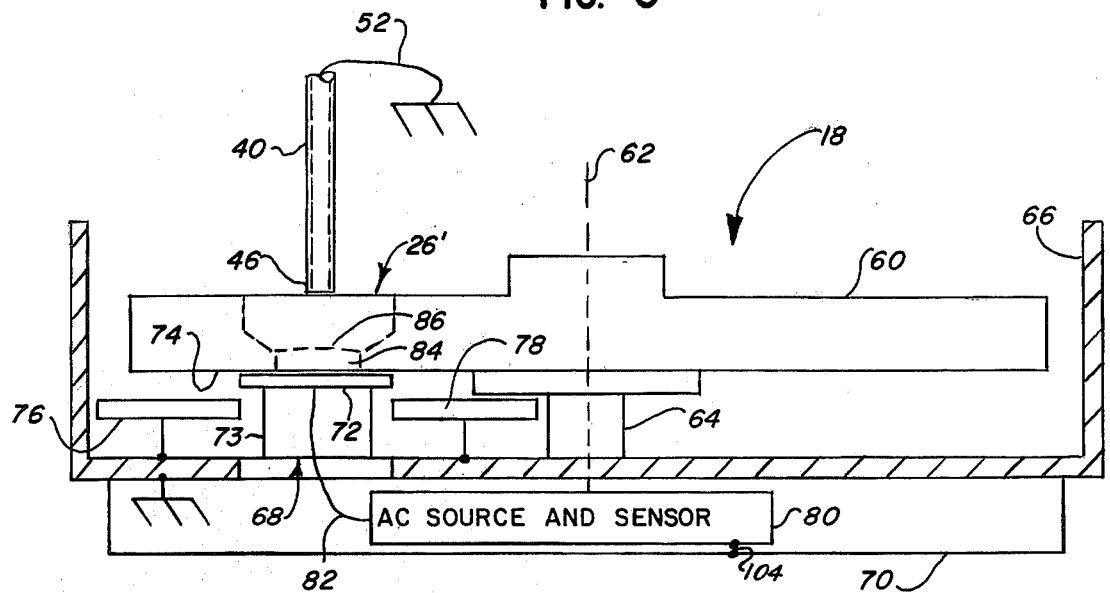
FIG. 3 is a more or less diagrammatic view partially in section of a sample fluid supply.

In FIG. 3, sample supply 18 includes supply tray 60 containing a plurality of supply cavities and, in particular, includes one supply cavity 26', which will be used for purposes of describing the present invention. Sample supply tray 60 is rotatable about a central axis 62 and is made of an insulating or dielectric material such as a synthetic resin. Tray 60 is rotatably driven by drive means (not shown) through a shaft 64. Tray 60 is contained within a metal pan 66 which is open at the top and which is further provided with an opening 68 in the bottom thereof. A metal shield 70 is provided under the bottom of pan 66.

An electrode 72 is carried by the pan 66 by support 73, but is electrically insulated therefrom. Electrode 72 is biased against and engaged against the bottom 74 of sample tray 60 by such as the support 73 being a spring and is retained in position so that as tray 60 rotates, electrode 72 slides across the bottom of tray 60 and maintains its position relative to pan 66.

The position of electrode 72 is directly under the sample probe 28 when sample probe 28 is aspirating an aliquot from the sample supply 18.

Field deflector plates 76 and 78 are carried by pan 66 and are retained in fixed position relative to electrode 72. Field deflector plates 76 and 78 are electrically conductive and are electrically connected to the pan 66. Field deflector plates 76 and 78 are closely spaced from electrode 72 below tray 60 and form a ground plane to deflect any electromagnetic radiation from electrode 72 downwardly. Pan 66 and deflector plates 76 and 78 are electrically connected to a signal ground as is tube 40 through lead 52. An AC source and sensor 80 is located between the shield 70 and the bottom of pan 66. The AC source and sensor 80 is connected to electrode 72 by way of lead 82. Supply cavity 26' includes a fluid sample 84 having a top surface 86.

Figure 4:
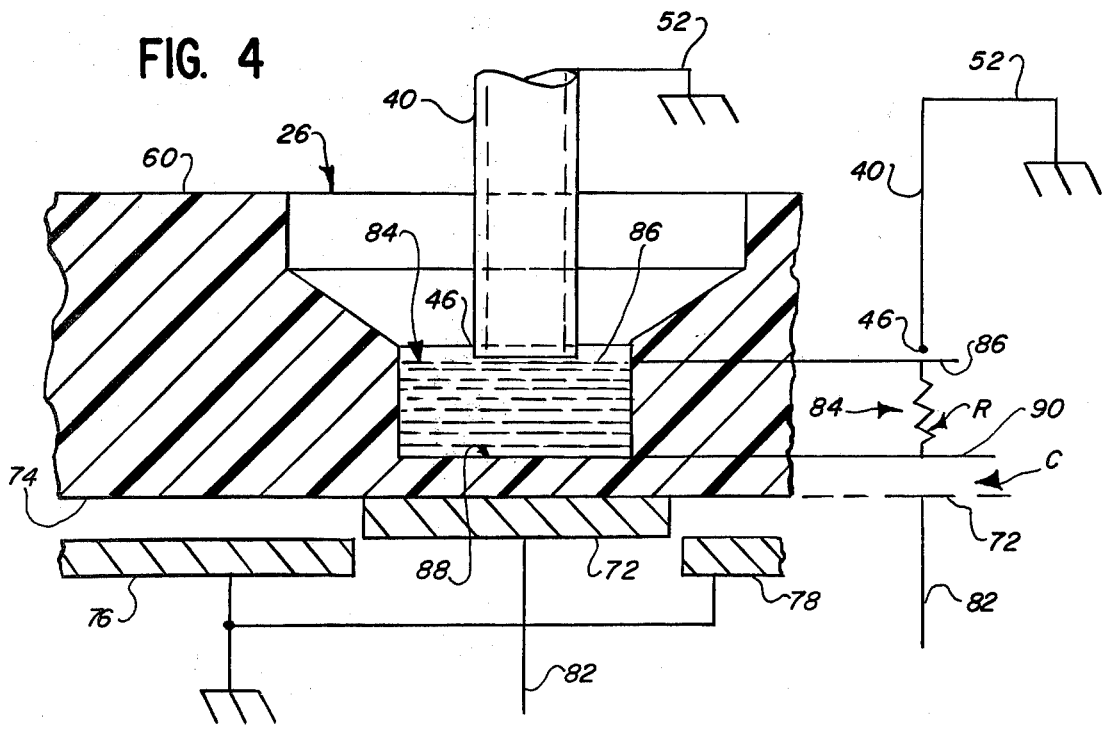
FIG. 4 is a fragmentary vertical sectional view of a portion of the sample fluid supply illustrating the electrical equivalents of the illustrated supply structure.

In FIG. 4, the vertical thickness of sample fluid 84 is represented electrically by a resistance R. The bottom surface 88 of sample fluid 84 corresponds to the bottom surface of the supply cavity 26' and effectively forms a plate 90 of a capacitor C. The electrode 72 forms the other plate of the capacitor C, and the thickness of supply tray 60 between bottom surface 86 and electrode 72 forms the dielectric of the capacitor C. The plate 90 of capacitor C is or will be connected to circuit ground through resistance R, tube 40 and lead 52 when the bottom tip 46 of tube 40 touches or contacts the top surface of sample fluid 84. This effectively grounds any AC (alternating current) signal present on electrode 72 and changes or modulates the characteristics of any AC signal present thereon.

This physical arrangement of elements and the resulting connection of the electrical circuit represented thereby provides a structure in which the contact of the bottom tip 46 with sample fluid 84 may precisely and repeatably be determined. The field deflector plates 76 and 78 draw or deflect any electro-magnetic field generated by the AC signal applied to electrode 72 downwardly and outwardly. This reduces interference with that electromagnetic field by any stray capacitance which may occur above sample tray 60 such as an operator passing their hand over tray 60. Probe 28 by way of lead 52 is connected to signal ground, which aids in grounding any stray electromagnetic fields which may occur above sample tray 60.

The AC signal applied to electrode 72 is in protected environment above shield 70 and below metal pan 66 to reduce the effect of stray capacitances and electro-magnetic fields acting thereon, and the AC source and sensor 80 is located close to probe 72 to reduce losses in lead 82 which may occur in such as a coaxial cable. Moreover, the value of the capacitance C does not change significantly with a change in the amount of sample fluid contained in a sample cavity 26'.

Figure 5:
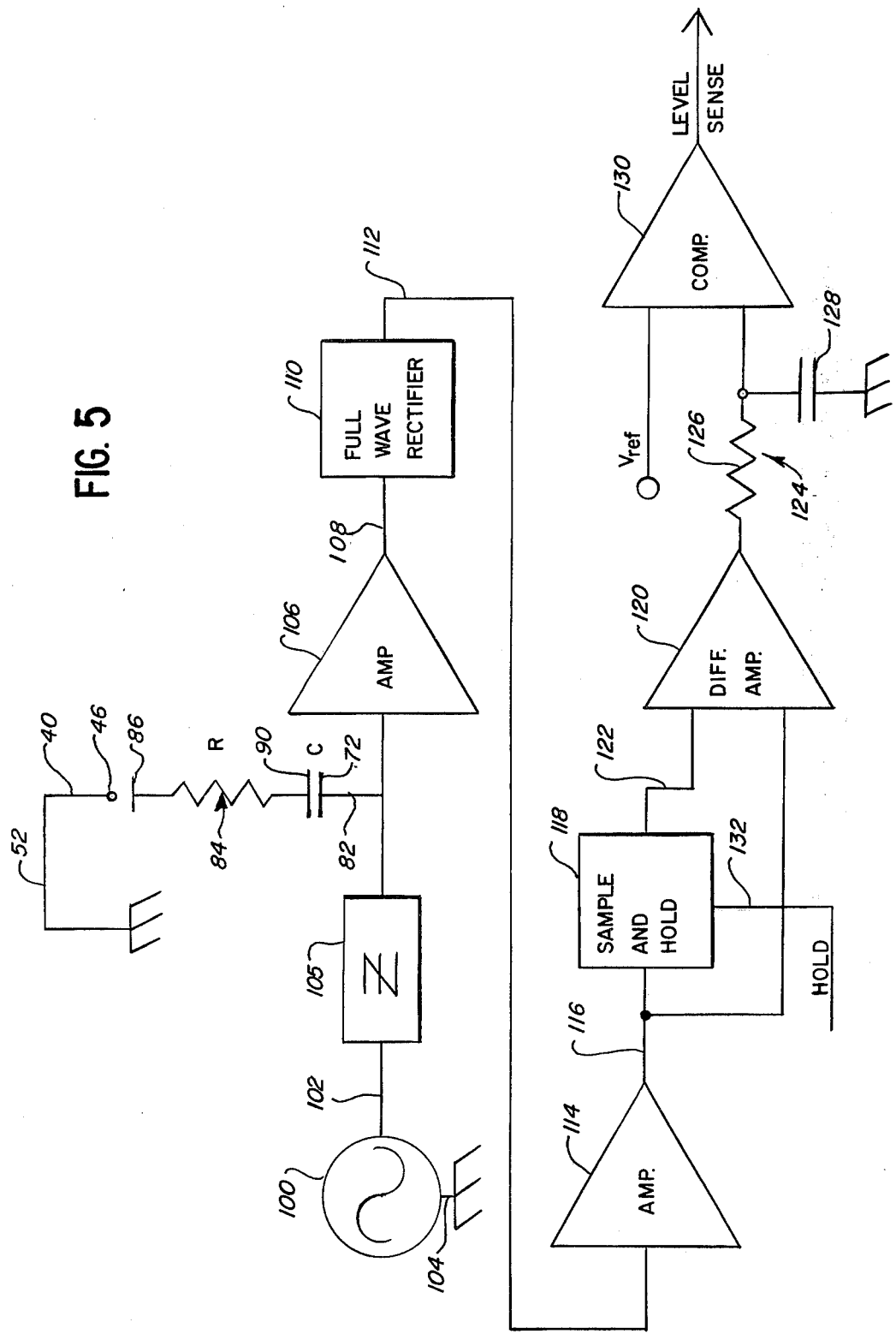
FIG. 5 is a schematic block diagram of the AC signal source and sensor of the invention.

In FIG. 5, an AC signal source 100 provides an AC signal on lead 102 relative to a signal ground connected to the source 100 by lead 104. The AC signal on lead 102 is applied through an impedance Z 105 to the lead 82 extending both to electrode 72 of capacitor C and to the input of amplifier 106. The input of amplifier 106 has a high impedance. The output of amplifier 106 occurring on lead 108 is applied to a full wave rectifier 110.

As in FIG. 4, the electrical equivalents of the structural elements are illustrated connected with electrode 82.

When bottom tip 46 of tube 40 is spaced from the top surface 86 of the sample fluid 84, the AC signal on lead 82 will have one voltage value. This one voltage value will be sensed by high input impedance amplifier 106 and will form a no contact DC (direct current) voltage level at the output on lead 112 of full wave rectifier 110. When the bottom tip of tube 40 just touches the top surface 86 of sample fluid 84, the AC signal on lead 82 is grounded through capacitance C, resistance R, tube 40 and lead 52 and the AC signal changes its voltage to another value. This other voltage value is sensed by amplifier 106 and results in a different or contact DC voltage level at the output 112 of full wave rectifier 110.

The output of full wave rectifier 110 is amplified in amplifier 114, the output of which on lead 116 is applied to both a sample and hold circuit 118 and one input of a differential amplifier 120. The output of the sample and hold circuit 118 is applied by way of lead 122 to the other input of differential amplifier 120. The output of differential amplifier 120 is applied through a low pass filter 124 comprised of a resistance 126 and capacitance 128 to one input of a comparator 130. Low pass filter 124 is used to remove unwanted electrical noise such as is produced from the vertical and horizontal drive means. The other input of comparator 130 is connected to a reference voltage $V_{REF}$ and comparator 130 performs the function of level shifting to provide logic compatible voltage levels. The output of comparator 130 provides a signal LEVEL SENSE, which indicates when the tip 46 has touched the top surface 86 of the fluid sample 84.

While the fluid probe 28 is performing one of the operations other than aspirating a sample fluid, the sample and hold circuit 118 passes the signal on lead 116 directly to lead 122. This is in response to a HOLD signal occurring on lead 132. Thus, the amplified DC voltage level from full wave rectifier 110 is applied to both of the inputs of differential amplifier 120 and the output on differential amplifier 120 indicates no contact.

During the aspirate operation or step in which a sample is to be aspirated from sample fluid 84, a HOLD signal is formed which enables the sample and hold circuit 118 and maintains the no contact voltage level on lead 122. Providing the HOLD signal only at this time avoids invalid level sensing during the other steps. When the bottom tip 46 of probe 28 contacts the top surface 86 of sample fluid 84, the amplified voltage on lead 116 changes to a contact value and differential amplifier 120 senses a difference in voltage levels supplied to its inputs. Differential amplifier 120 then outputs a signal indicating contact, which is level shifted through comparator 130 to provide the signal LEVEL SENSE. This LEVEL SENSE signal then is used by the control circuitry of analyzer 10 to stop the downward movement of fluid probe 28 so that tip 46 will not be immersed in sample fluid 84.

In one embodiment, fluid probe 28 is aspirating fluid samples of about 2 to 5 microliters from a supply cavity containing about 20 to 25 microliters of sample fluid. This relates to a change in about 10 picofarads of capacitance which must be sensed to determine when tip 46 touches top surface 86.

The present invention does not change the capacitance values which must be sensed to determine contact, but provides an arrangement of structural and circuit elements which provides for the precise and repeatable sensing of the probe and sample fluid contact.

Modifications and variations of the present invention are possible in light of the above teachings. It is therefore to be understood that within the scope of the appended claims, the invention may be practiced otherwise than as specifically described.

What is claimed and desired to be secured by Letters Patent of the United States is:

1. A level sensor for use in a fluid transfer mechanism transferring aliquots of electrically conductive sample fluids from a supply to reaction vessels, the mechanism including an arm, a shaft having an axis aligned vertically and being coupled to one end of the arm, a vertical drive means for moving the arm up and down along the shaft axis, horizontal drive means for rotating the arm in an arcuate path around the shaft axis and fluid probe means depending from the other end of the arm for aspirating the aliquot from the sample supply and dispensing the aspirated aliquot in the reaction vessel, the level sensor comprising:

a supply tray formed of a dielectric material, the tray including individual supply cavities which contain the sample fluids, the tray being rotatable to align an individual cavity with the arcuate path and when so aligned the individual cavity receiving the probe means during the aspiration of the aliquot;

an electrode engaged against said supply tray in a position under said individual cavity, the electrode, the dielectric material of the sample tray and the electrically conductive sample fluid forming a capacitor;

AC signal means connected to the electrode and supplying an AC signal thereto relative to a signal ground;

sensor means connected to the electrode for sensing a modulation of the AC signal and providing a level sense signal in response thereto; and the probe means being connected to the signal ground, so that when the probe means engage the sample fluid in the supply cavity, the AC signal applied to the electrode is modulated by the capacitive grounding of the electrode through the sample tray dielectric material, the sample fluid and the probe means to ground and thereby generating the level sense signal.

2. The level sensor as claimed in claim 1 in which there are field deflector means adjacent the electrode under the tray for deflecting any electromagnetic radiation of the electrode downwardly.

3. The level sensor as claimed in claim 2 in which the field deflector means are connected to signal ground.

4. The level sensor as claimed in claim 1 in which the AC signal means include a source providing the AC signal through a high impedance to the electrode.

5. The level sensor as claimed in claim 1 in which the sensor means include a high impedance input amplifier sensing the AC signal on the electrode.

6. The level sensor as claimed in claim 1 in which the sensor means include rectifier means for converting the sensed AC signal to a DC voltage value.

7. The level sensor as claimed in claim 6 in which the sensor means include sample and hold means for maintaining on its output the DC voltage value occurring prior to an aspirate operation during an aspirate operation and differential amplifier means receiving both the DC voltage value from the rectifier means and the maintained DC voltage value to determine when the DC voltage values change and to output a level sense signal at the change.

8. The level sensor as claimed in claim 7 in which the sensor means include low pass filter means connected to the output of the differential amplifier means to filter high frequency electrical noise from the vertical and horizontal drive means.

9. The level sensor as claimed in claim 8 in which the sensor means include a level shifter for shifting the signal from the low pass filter means to logic compatible levels.

10. A level sensor for determining when a probe contacts the atmosphere-liquid interface of a conductive sample fluid, the sensor comprising a sample supply vessel open to the atmosphere at its upper end and containing the sample fluid, the sample supply vessel being formed of a dielectric material and having an exterior surface on its bottom end, the vessel receiving the probe through the open upper end;

an electrode engaged against said exterior surface, the electrode, the dielectric material of the sample tray and the conductive sample fluid forming a capacitor;

AC signal means connected to the electrode and supplying an AC signal thereto relative to a signal ground;

sensor means connected to the electrode for sensing modulation of the AC signal and providing a level sense signal in response thereto; and the probe being connected to the signal ground such that when the probe engages the atmosphere-liquid interface of the sample fluid in the supply vessel, the AC signal applied to the electrode is modulated by the capacitive grounding of the electrode through the sample tray dielectric material, the sample fluid and the probe conductance to ground and thereby generating the level sense signal.

11. The level sensor as claimed in claim 10 in which there are field deflector means adjacent the electrode under the supply vessel for deflecting an electromagnetic radiation of the electrode downwardly.

12. The level sensor as claimed in claim 11 in which the field deflector means are connected to signal ground.

13. The level sensor as claimed in claim 10 in which the AC signal means include a source providing the AC signal through a high impedance to the electrode.

14. The level sensor as claimed in claim 10 in which the sensor means include a high impedance input amplifier sensing the AC signal on the electrode.

15. The level sensor as claimed in claim 10 in which the sensor means include rectifier means for converting the sensed AC signal to a DC voltage value.

16. The level sensor as claimed in claim 15 in which the sensor means include sample and hold means for maintaining on its output the DC voltage value occurring prior to an aspirate operation during an aspirate operation and differential amplifier means receiving both the DC voltage value from the rectifier means and the maintained DC voltage value to determine when the DC voltage values change and to output a level sense signal at the change.

17. The level sensor as claimed in claim 16 in which the sensor means include low pass filter means connected to the output of the differential amplifier means to filter high frequency electrical noise.

18. The level sensor as claimed in claim 17 in which the sensor means include a level shifter for shifting the signal from the low pass filter means to logic compatible levels.

19. A method of sensing the level of a sample fluid in a fluid transfer mechanism transferring aliquots of electrically conductive sample fluids from a supply to reaction vessels, the mechanism including an arm, a shaft having an axis aligned vertically and being coupled to one end of the arm, vertical drive means for moving the arm up and down along the shaft axis, horizontal drive means for rotating the arm in an arcuate path around the shaft axis and fluid probe means depending from the other end of the arm for aspirating the aliquot from the sample supply and dispensing the aspirated aliquot in the reaction vessel, the method comprising:
  forming a supply tray of a dielectric material, to include individual supply cavities which contain the fluid samples, the tray being rotatable to align an individual cavity with the arcuate path and when so aligned the individual supply cavity adopted to receive the probe means during the aspiration of the aliquot;
  forming a capacitor of the sample fluid, the dielectric material and an electrode by biasing the electrode against the supply tray in a position under said individual supply cavity;
  applying an AC signal to the electrode relative to a signal ground;
  sensing modulation of the AC signal applied to the electrode and providing a level sense signal when the modulation is sensed;
  connecting the probe means to the signal ground; and
  modulating the AC signal applied to the electrode by engaging the fluid sample in the cavity with the probe means capacitively to ground the AC signal applied to the electrode through said capacitor and grounded probe means.

20. The method as claimed in claim 19 which includes deflecting any electromagnetic radiation of the electrode downwardly.

21. The method as claimed in claim 20 in which deflecting any radiation includes forming a ground plane adjacent the electrode below the supply tray.

22. The method as claimed in claim 19 in which applying the AC signal includes applying the AC signal through a high impedance.

23. The method as claimed in claim 19 in which sensing the AC signal includes sensing with a high impedance input.

24. The method as claimed in claim 19 which sensing modulation of the AC signal includes rectifying the sensed AC signal to a DC voltage value.

25. The method as claimed in claim 24 in which sensing the AC signal includes holding the DC voltage value occurring prior to an aspirate operation, during an aspirate operation and producing a level sense signal when the held voltage value differs from the rectified DC voltage value.

26. The method as claimed in claim 25 in which the sensing includes low pass filtering the level sense signal.

27. The method as claimed in claim 26 in which the sensing includes level shifting the filtered level sense signal to logic compatible levels.

28. A method of sensing the contact of a probe with the atmosphere-liquid interface of a conductive sample fluid, the method comprising:
  forming a capacitor of the conductive sample fluid, a dielectric supply vessel containing the sample fluid and an electrode engaged against the vessel with the atmosphere-liquid interface of the sample fluid being opposite the electrode;
  applying an AC signal relative to ground to the electrode;
  sensing modulation of the AC signal applied to the electrode and providing a level sense signal in response thereto;
  connecting the probe to the signal ground; and
  modulating the AC signal applied to the electrode by engaging the fluid sample in the vessel with the probe to capacitively ground the AC signal applied to the electrode through said capacitor and grounded probe.

29. The method as claimed in claim 28 which includes deflecting any electromagnetic radiation of the electrode downwardly.

30. The method as claimed in claim 29 in which deflecting any radiation includes forming a ground plane adjacent the electrode below the supply vessel.

31. The method as claimed in claim 28 in which applying the AC signal includes applying the AC signal through a high impedance.

32. The method as claimed in claim 28 in which sensing the AC signal includes sensing with a high impedance input.

33. The method as claimed in claim 28 in which sensing modulation of the AC signal includes rectifying the sensed AC signal to a DC voltage value.

34. The method as claimed in claim 33 in which sensing the AC signal includes holding the DC voltage value occurring prior to an aspirate operation during as aspirate operation and producing a level sense signal when the held voltage value differs from the rectified DC voltage value.

35. The method as claimed in claim 34 in which the sensing includes low pass filtering the level sense signal.

36. The method as claimed in claim 35 in which the sensing includes level shifting the filtered level sense signal to logic compatible levels.

* * * * *

UNITED STATES PATENT AND TRADEMARK OFFICE
CERTIFICATE OF CORRECTION

PATENT NO. : 4,326,851
DATED : April 27, 1982
INVENTOR(S) : Bello et al.

It is certified that error appears in the above-identified patent and that said Letters Patent are hereby corrected as shown below:

Column 6, line 6, before "protected" insert --a--.

Column 8, line 67, change "an" to --any--.

Signed and Sealed this

Fourteenth Day of December 1982

[SEAL]

Attest:

GERALD J. MOSSINGHOFF

Attesting Officer      Commissioner of Patents and Trademarks